(12) United States Patent
Bonner et al.

(10) Patent No.: US 12,246,181 B2
(45) Date of Patent: Mar. 11, 2025

(54) DUAL CHAMBER PACING

(71) Applicant: Medtronic, Inc., Minneapolis, MN (US)

(72) Inventors: Matthew D. Bonner, Plymouth, MN (US); Kathryn Hilpisch, Cottage Grove, MN (US); Kaileigh E. Rock, Saint Paul, MN (US); Jean M. Carver, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 458 days.

(21) Appl. No.: 17/653,959

(22) Filed: Mar. 8, 2022

(65) Prior Publication Data

US 2022/0314001 A1    Oct. 6, 2022

Related U.S. Application Data

(60) Provisional application No. 63/170,051, filed on Apr. 2, 2021.

(51) Int. Cl.
*A61N 1/368* (2006.01)
*A61N 1/05* (2006.01)

(52) U.S. Cl.
CPC ......... *A61N 1/3684* (2013.01); *A61N 1/0573* (2013.01)

(58) Field of Classification Search
CPC ............... A61N 1/3684; A61N 1/0573; A61N 1/37518; A61N 1/3756; A61N 1/372; A61N 1/37512
See application file for complete search history.

(56) References Cited

U.S. PATENT DOCUMENTS 3,814,104 A    6/1974   Irnich et al.
3,835,864 A    9/1974   Rasor et al.
(Continued)

FOREIGN PATENT DOCUMENTS

WO    2002022202 A2    3/2002
WO    2006118865 A2    11/2006
(Continued)

OTHER PUBLICATIONS

Hayes, "Advances in pacing therapy for bradycardia", International Journal of Cardiology, vol. 32, Elsevier Science Publishers B.V., Apr. 1, 1991, pp. 183-196.
(Continued)

*Primary Examiner* — Gary Jackson
*Assistant Examiner* — Sebastian X Lukjan
(74) *Attorney, Agent, or Firm* — Shumaker & Sieffert, P.A.

(57) ABSTRACT

A medical system includes an implantable medical device that carries a first electrode on a distal end of the implantable medical device and a return electrode. The implantable medical device is configured to be positioned within a heart. The implantable medical device further includes a leadlet including a proximal end and a distal end. The proximal end is attached to the implantable medical device, and the distal end is configured to penetrate tissue of the heart. The leadlet carries a second electrode, and a body of the leadlet between the proximal end and the distal end is configured to flex when the distal end is implanted in the tissue of the heart. The implantable medical device further includes a fixation device attached to the implantable medical device. The fixation device is configured to affix the distal end of the implantable medical device to the heart.

20 Claims, 7 Drawing Sheets

(56) References Cited

U.S. PATENT DOCUMENTS

| | | | |
|---|---|---|---|
| 3,943,936 | A | 3/1976 | Rasor et al. |
| 4,103,690 | A | 8/1978 | Harris |
| 4,142,530 | A | 3/1979 | Wittkampf |
| 4,256,115 | A | 3/1981 | Bilitch |
| 4,269,198 | A | 5/1981 | Stokes |
| 4,280,512 | A | 7/1981 | Karr et al. |
| 4,858,623 | A | 8/1989 | Bradshaw et al. |
| 4,936,823 | A | 6/1990 | Colvin |
| 5,193,540 | A | 3/1993 | Schulman et al. |
| 5,411,535 | A | 5/1995 | Fujii et al. |
| 5,487,758 | A | 1/1996 | Hoegnelid et al. |
| 5,573,540 | A | 11/1996 | Yoon |
| 5,674,259 | A | 10/1997 | Gray |
| 5,683,447 | A | 11/1997 | Bush et al. |
| 6,007,558 | A | 12/1999 | Ravenscroft et al. |
| 6,151,525 | A | 11/2000 | Soykan et al. |
| 6,212,434 | B1 | 4/2001 | Scheiner |
| 6,240,322 | B1 | 5/2001 | Peterfeso et al. |
| 6,286,512 | B1 | 9/2001 | Loeb et al. |
| 6,409,674 | B1 | 6/2002 | Brockway et al. |
| 6,575,967 | B1 | 6/2003 | Leveen et al. |
| 6,643,546 | B2 | 11/2003 | Mathis et al. |
| 6,783,499 | B2 | 8/2004 | Schwartz |
| 6,915,149 | B2 | 7/2005 | Ben-Haim |
| 6,978,178 | B2 | 12/2005 | Sommer et al. |
| 7,082,335 | B2 | 7/2006 | Klein et al. |
| 7,139,614 | B2 | 11/2006 | Scheiner et al. |
| 7,290,743 | B2 | 11/2007 | Nowack |
| 7,412,289 | B2 | 8/2008 | Malonek et al. |
| 7,418,298 | B2 | 8/2008 | Shiroff et al. |
| 7,813,805 | B1 | 10/2010 | Farazi |
| 8,353,940 | B2 | 1/2013 | Benderev |
| 8,781,605 | B2 | 7/2014 | Bornzin et al. |
| 9,017,341 | B2 | 4/2015 | Bornzin et al. |
| 9,039,594 | B2 | 5/2015 | Annest et al. |
| 9,597,514 | B2 | 3/2017 | Khairkhahan et al. |
| 9,901,732 | B2 | 2/2018 | Sommer et al. |
| 10,039,922 | B2 | 8/2018 | Regnier |
| 10,159,834 | B2 | 12/2018 | Drake et al. |
| 10,406,370 | B1 | 9/2019 | Makharinsky |
| 10,413,720 | B2 | 9/2019 | Nuta et al. |
| 10,493,284 | B2 | 12/2019 | Ortega et al. |
| 10,729,902 | B1 | 8/2020 | Makharinsky et al. |
| 10,792,080 | B2 | 10/2020 | Raina et al. |
| 11,331,475 | B2 | 5/2022 | Drake et al. |
| 2002/0103424 | A1 | 8/2002 | Swoyer et al. |
| 2002/0165589 | A1 | 11/2002 | Imran et al. |
| 2003/0060866 | A1 | 3/2003 | Schmidt |
| 2003/0088301 | A1 | 5/2003 | King |
| 2004/0122456 | A1 | 6/2004 | Saadat et al. |
| 2004/0147973 | A1 | 7/2004 | Hauser |
| 2004/0230281 | A1 | 11/2004 | Heil et al. |
| 2006/0084965 | A1 | 4/2006 | Young |
| 2006/0085039 | A1 | 4/2006 | Hastings et al. |
| 2006/0085041 | A1 | 4/2006 | Hastings et al. |
| 2006/0224224 | A1 | 10/2006 | Muhlenberg et al. |
| 2007/0179552 | A1 | 8/2007 | Dennis et al. |
| 2009/0082828 | A1 | 3/2009 | Ostroff |
| 2010/0145382 | A1 | 6/2010 | Chanduszko |
| 2010/0318172 | A1 | 12/2010 | Schaefer |
| 2012/0172892 | A1 | 7/2012 | Grubac et al. |
| 2014/0039591 | A1 | 2/2014 | Drasler et al. |
| 2014/0066895 | A1 | 3/2014 | Kipperman |
| 2014/0107723 | A1 | 4/2014 | Hou et al. |
| 2015/0039070 | A1 | 2/2015 | Kuhn et al. |
| 2015/0335894 | A1 | 11/2015 | Bornzin et al. |
| 2017/0326369 | A1 | 11/2017 | Koop et al. |
| 2018/0050208 | A1 | 2/2018 | Shuros et al. |
| 2019/0083779 | A1 | 3/2019 | Yang et al. |
| 2019/0111265 | A1 | 4/2019 | Zhou |
| 2019/0111270 | A1 | 4/2019 | Zhou |
| 2019/0143118 | A1 | 5/2019 | Bullinga |
| 2019/0192863 | A1 | 6/2019 | Koop et al. |
| 2019/0209845 | A1 | 7/2019 | Stadler et al. |
| 2019/0232053 | A1 | 8/2019 | Yang et al. |
| 2019/0269420 | A1 | 9/2019 | Matusaitis et al. |
| 2019/0351236 | A1* | 11/2019 | Koop ................... A61N 1/3756 |
| 2019/0374254 | A1 | 12/2019 | Arevalos et al. |
| 2020/0229805 | A1 | 7/2020 | Gammie et al. |
| 2020/0229806 | A1 | 7/2020 | Goldfarb et al. |
| 2020/0261725 | A1 | 8/2020 | Yang et al. |
| 2020/0261734 | A1 | 8/2020 | Yang et al. |
| 2020/0289829 | A1 | 9/2020 | Ghosh |
| 2020/0306522 | A1 | 10/2020 | Chen et al. |
| 2020/0306530 | A1 | 10/2020 | Koop et al. |
| 2020/0353249 | A1* | 11/2020 | Min ..................... A61N 1/371 |
| 2020/0353265 | A1 | 11/2020 | Ghosh et al. |
| 2020/0398045 | A1 | 12/2020 | Anderson et al. |
| 2021/0046306 | A1 | 2/2021 | Grubac et al. |
| 2021/0187307 | A1 | 6/2021 | Ries et al. |
| 2022/0387764 | A1 | 12/2022 | Bonner et al. |
| 2023/0012417 | A1 | 1/2023 | Rock et al. |

FOREIGN PATENT DOCUMENTS

| | | |
|---|---|---|
| WO | 2018097826 A1 | 5/2018 |
| WO | 2020023406 A1 | 1/2020 |
| WO | 2020076833 A1 | 4/2020 |
| WO | 2020163031 A1 | 8/2020 |

OTHER PUBLICATIONS

Petrie, "Permanent Transvenous Cardiac Pacing", Clinical Techniques in Small Animal Practice, Elsevier Inc., 2005, pp. 164-172, (Applicant points out, in accordance with MPEP 609.04(a), that the year of publication, 2005, is sufficiently earlier than the effective U.S. filing date, so that the particular month of publication is not an issue.).

U.S. Appl. No. 17/805,450, filed Jun. 3, 2022, naming inventors Matthew D. Bonner et al.

Austin et al., "Innovative pacing: Recent advances, emerging technologies, and future directions in cardiac pacing", Trends in Cardiovascular Medicine, vol. 26, Mayo Clinic Florida, 2016, pp. 452-463, (Applicant points out, in accordance with MPEP 609.04(a), that the year of publication, 2016, is sufficiently earlier than the effective U.S. filing date, so that the particular month of publication is not an issue.).

Haqqani et al., "The Implantable Cardioverter-Defibrillator Lead: Principles, Progress and Promises," PACE, vol. 32, Oct. 2009, pp. 1336-1353.

Mulpuru et al., "Cardiac Pacemakers: Functions, Troubleshooting, and Management", Journal of the American College of Cardiology, vol. 69, No. 2, Oct. 18, 2016, pp. 189-210.

Prosecution History from U.S. Appl. No. 17/191,071, dated Jun. 9, 2022 through Jul. 31, 2023, 34 pp.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

* cited by examiner

DUAL CHAMBER PACING

This application claims the benefit of U.S. Provisional Application Ser. No. 63/170,051 (filed Apr. 2, 2021), which is entitled, "DUAL CHAMBER PACING" and is incorporated by reference herein in its entirety.

TECHNICAL FIELD

This disclosure relates to implantable medical systems.

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach, endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads (e.g., distal portions of elongated implantable medical leads) may be implanted at target locations selected to detect a physiological condition of the patient and/or deliver one or more therapies. For example, implantable medical leads may be delivered to locations within an atrium or ventricle to sense intrinsic cardiac signals and deliver pacing or antitachyarrhythmia shock therapy from a medical device coupled to the lead. In other examples, implantable medical leads may be tunneled to locations adjacent a spinal cord or other nerves for delivering pain therapy from a medical device coupled to the lead. Implantable medical leads may include fixation components to secure a distal end of the lead at the target location.

Some cardiac pacemakers are sized to be completely implanted within one of the chambers of the heart, and may include electrodes integrated with or attached to the device housing rather than leads. Such cardiac pacemakers may include fixation components to secure the pacemaker to cardiac tissue at a target location. Some cardiac pacemakers provide dual chamber functionality, by sensing and/or stimulating the activity of both atria and ventricles, or other multi-chamber functionality. A cardiac pacemaker may provide multi-chamber functionality via leads that extend to respective heart chambers, or multiple cardiac pacemakers may provide multi-chamber functionality by being implanted in respective chambers.

SUMMARY

In an example, a medical system includes: an implantable medical device that carries a first electrode on a distal end of the implantable medical device and a return electrode, wherein the implantable medical device is configured to be positioned within a heart; a leadlet including a proximal end and a distal end, wherein the proximal end is attached to the implantable medical device, wherein the distal end is configured to penetrate tissue of the heart, wherein the leadlet carries a second electrode, and wherein a body of the leadlet between the proximal end and the distal end is configured to flex when the distal end is implanted in the tissue of the heart; and a fixation device attached to the implantable medical device, wherein the fixation device is configured to affix the implantable medical device to the heart.

In an example, a medical system includes: an implantable medical device including a housing, wherein the housing carries a first electrode on a distal end of the housing, and wherein the housing carries one or more return electrodes, wherein the housing is configured to be positioned within a heart; a leadlet including a proximal end and a distal end, wherein the proximal end is attached to the housing, wherein the distal end is configured to penetrate tissue of the heart, wherein the leadlet carries a second electrode, and wherein a body of the leadlet between the proximal end and the distal end is configured to flex when the distal end is implanted in the tissue of the heart; circuitry supported by the housing, wherein the circuitry is configured to deliver stimulation signals to the heart using the one or more return electrodes and at least one of the first electrode or the second electrode; and a fixation device attached to the implantable medical device, wherein the fixation device is configured to affix the distal end of the implantable medical device to the heart.

In an example, a method includes: affixing, using a fixation device, an implantable medical device to a heart, wherein the implantable medical device carries a first electrode and a return electrode, wherein the implantable medical device is configured to be positioned within the heart; and penetrating, using a distal end of a leadlet, tissue of the heart, wherein a proximal end of the leadlet is attached to the implantable medical device, wherein a body of the leadlet between the proximal end and the distal end is configured to flex when the distal end is implanted in the tissue of the heart, and wherein the leadlet carries a second electrode.

The details of one or more examples are set forth in the accompanying drawings and the description below. Other features, objects, and advantages will be apparent from the description and drawings, and from the claims.

DETAILED DESCRIPTION

This disclosure describes a medical system configured to position one or more electrodes within a heart. The medical system includes an implantable medical device ("IMD") configured to be positioned within the heart. A leadlet extends from the IMD. The IMD includes therapy delivery circuitry configured to provide stimulation signals via a first electrode on a distal end of the IMD and a second electrode carried by a leadlet. The leadlet is configured to flex to facilitate positioning of the leadlet in the heart as well as allow the leadlet to flex during movements of the heart. Further, a body of the leadlet between a proximal end and a distal end of the leadlet is configured to stiffen (e.g., during implantation of the distal end of the leadlet into tissues of the heart) to facilitate implantation of the leadlet into the heart.

For example, the IMD may be configured to implant an electrode in the left ventricular (LV) septum while the IMD is implanted in the right atrium (RA). Implanting the IMD may cause the first electrode carried by the IMD (e.g., on the distal end of the IMD) to contact the atrial tissue of RA. At the same time, the leadlet may penetrate the tissue of the RA such that the second electrode carried by the leadlet is implanted (e.g., embedded) in the LV septum. Due to the flexibility of the leadlet, a clinician may more advantageously negotiate positioning of the leadlet in the tissue.

In addition, the body of the leadlet may be configured to stiffen such that the leadlet more effectively penetrates the tissue, facilitating implantation of the leadlet. For example, the leadlet may be configured to receive a stylet that allows a clinician or another user to impart a distal force on the distal end of the leadlet causing the distal end to penetrate the ventricular tissue. Additionally or alternatively, the stylet may extend alongside the IMD and/or leadlet and directly mechanically communicate with (e.g., connect to, be mechanically coupled to, etc.) the second electrode carried by the leadlet. After removal of the stylet, the leadlet may again flex (e.g., between the distal end of the leadlet anchored in the ventricular tissue and the distal end of the IMD affixed to atrial tissue) to allow the leadlet to flex during movements of the heart.

By implanting the IMD in the RA and the leadlet in the LV septum, the first electrode may sense and delivery therapy signals to surface tissue of the RA while the second electrode senses and delivers therapy signals in the LV septum. That is, the first electrode may pace the RA while the second electrode paces the LV. In this way, the IMD may deliver dual chamber pacing while implanted in the RA.

In some examples, the leadlet may extend from a portion of the IMD (e.g., a housing wall, a distal end, a distal portion, a proximal end, a proximal portion, etc.). In examples, the leadlet extends from a distal end of the IMD. As described above, the leadlet may be configured to penetrate ventricular tissue of the LV when the distal end of the IMD is affixed to atrial tissue in the RA. The distal end of the IMD may include a fixation device to enable fixation of the IMD to the atrial tissue. For example, the fixation device may include one or more passive fixation tines to anchor the distal end of lead in ventricular tissue. As another example, the fixation device may include a helically-shaped fixation tine that is screwed into the atrial tissue.

Figure 1:
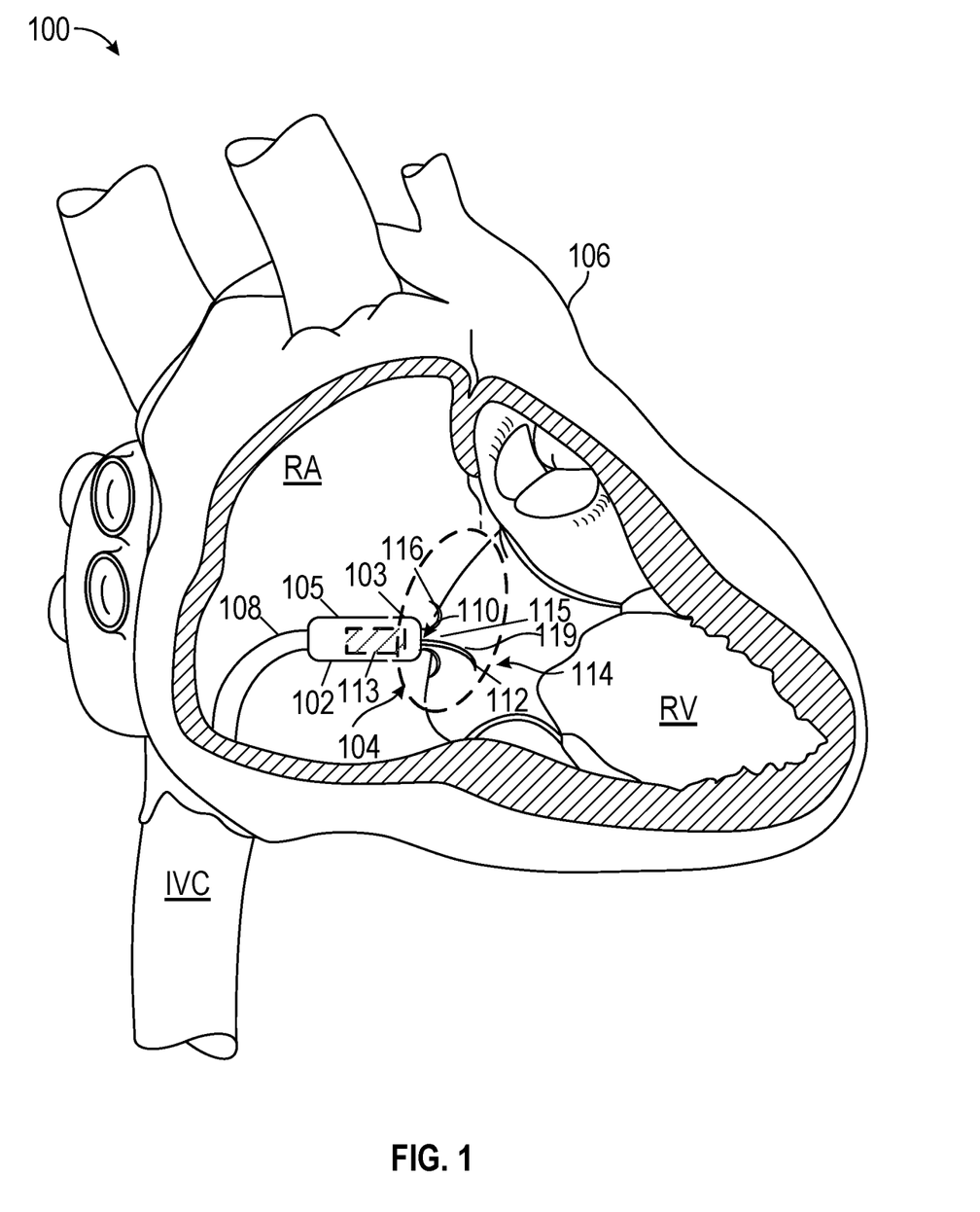
FIG. 1 is a conceptual diagram illustrating an example medical system and delivery catheter.

FIG. 1 is a conceptual diagram illustrating a portion of an example medical device system 100 configured to implant an implantable medical device 102 ("IMD 102") at a target implant site 104. In some examples, as illustrated in FIG. 1, the target implant site 104 may include an appendage or triangle of Koch region of a right atrium (RA) of a heart 106 of a patient. In some examples, target implant site 104 may include other portions of heart 106 or other locations within a body of the patient. Medical device system 100 may include a delivery catheter 108 configured to house and controllably deploy IMD 102. In some examples, a clinician may maneuver medical device system 100 to target implant site 104. For example, with the IMD loaded therein, the clinician may guide delivery catheter 108 up through the inferior vena cava (IVC) and into the RA of heart 106. In some examples, other pathways or techniques may be used to guide delivery catheter 108 into other target implant sites within the body of the patient.

Delivery catheter 108 may define a lumen ("delivery catheter lumen") configured to allow IMD 102 to translate through the delivery catheter lumen. Delivery catheter 108 may define a lumen opening to the delivery catheter lumen at a distal end of delivery catheter 108. The delivery catheter lumen and the lumen opening may be sized to allow IMD 102 to translate through the delivery catheter lumen and the lumen opening to position IMD 102 within or in the vicinity of target implant site 104.

Delivery catheter 108 may be configured to allow a clinician to deliver medical system 100 through a vena cava (e.g., the IVC) for implantation of IMD 102 within an atrium (e.g., the RA) of heart 106. Delivery catheter 108 may be intravenously transited through the IVC such that the catheter distal section passes into the RA. Delivery catheter 108 may be configured to deliver medical system 100 to the target implant site 104. In examples, delivery catheter 108 is configured to allow the clinician to position the catheter distal end in proximity to a target implant site 104 as the catheter distal section transitions from the vena cava (e.g., the IVC) into the atrium (e.g., RA). Target implant site 104 may include an appendage or triangle of Koch region of the RA, or some other portion of heart 106, or other locations within a body of a patient.

IMD 102 includes a fixation device 116 configured to engage tissue. Fixation device 116 is attached to IMD 102. Fixation device 116 may include, for example, one or more elongated tines such as fixation tines configured to substantially maintain an orientation of IMD 102 with respect to target implant site 104. Fixation device 116 may include fixation tines of any shape, including helically-shaped fixation tines. Fixation device 116 (e.g., fixation tines) may be configured to penetrate tissue in the vicinity of target implant site 104 to substantially maintain an orientation of IMD 102. For example, IMD 102 may include a housing 105 defining a distal end 103 of IMD 102 ("IMD distal end 103"), and fixation device 116 may be configured to affix IMD 102 to target implant site 104 by substantially affixing distal end 103 to the tissue. In examples, fixation device is attached to IMD distal end 103.

IMD 102 includes a first electrode 110 mechanically supported by housing 105. In examples, first electrode 110 is mechanically supported by IMD distal end 103. First electrode 110 may be electrically connected to circuitry 113 housed within IMD 102. Medical system 100 also includes a second electrode 112. Second electrode 112 may be electrically connected to circuitry 113 housed within IMD 102 via a leadlet 114. In examples, leadlet 114 carries and/or mechanically supports second electrode 112.

Leadlet 114 includes a proximal end attached to IMD 102. In examples, the proximal end is attached to IMD distal end 103. In other examples, the proximal end of leadlet 114 may be attached to a distal portion of IMD 102, a proximal end of IMD 102, a proximal portion of IMD 102, a housing wall of IMD 102, and/or the like. Leadlet 114 includes a distal end opposite the proximal end. The distal end of leadlet 114 may mechanically support second electrode 112. The distal end of leadlet 114 may be configured to penetrate tissues (e.g., atrial tissues) of heart 106. Leadlet 114 defines a body 119 of leadlet 114 ("leadlet body 119") between the proximal end and distal end of leadlet 114. Leadlet body 119 is configured to flex when the distal end is implanted within the tissue of heart 106. Leadlet body 119 may be configured to stiffen (e.g., during implantation of the distal end of the leadlet into tissues of the heart) to enable delivery of dual chamber pacing. Leadlet body 119 may have a length of from about 6 millimeters (mm) to about 20 mm, although other lengths are contemplated by this disclosure.

IMD 102 may be attached to atrial tissue (e.g., using fixation device 116) to place first electrode 110 in contact with the atrial tissue of the RA. To enable the delivery of dual chamber pacing, leadlet 114 may penetrate the tissue from the RA to embed (e.g., implant) second electrode 112 into the LV septum. Leadlet 114 may be configured to flex with movement of heart 106 when second electrode 112 is implanted in the LV septum. For example, at least a portion of leadlet body 119 may flex. In examples, fixation device 116 is configured to substantially maintain an orientation of first electrode 110 with respect to target implant site 104 when fixation device 116 engages tissue. In examples, fixation device 116 may be configured to substantially maintain contact between first electrode 110 and tissues within target implant site 104 when fixation device 116 engages the tissue.

First electrode 110 and second electrode 112 may be configured to receive stimulation signals from IMD 102 for delivery to tissues of heart 106, as well as allow IMD 102 to sense electrical signals from heart 106. In examples, first electrode 110 and/or second electrode 112 may be a shallow electrode configured for sensing and delivery of therapy signals to tissue in a substantially non-invasive manner. In other examples, first electrode 110 and/or second electrode 112 may be a deep electrode configured to penetrate the tissues for sensing and delivery of therapy signals. Medical system 100 may include any number of electrodes in any configuration, including one or more electrodes supported by IMD 102 and/or leadlet 114.

Leadlet 114 may be configured to stiffen such that leadlet 114 more effectively penetrates the tissue, facilitating implantation of leadlet 114. For example, leadlet 114 may be configured to receive a stylet (or any other elongate member that leadlet 114 is configured to receive) to allow a user (e.g., a clinician) to position the distal end of leadlet 114 within the ventricular tissue of heart 106. Leadlet 114 may be configured such that a distal force imparted on the stylet applies a distal force on the distal end of leadlet 114. For example, leadlet 114 may define a bearing structure (e.g., a casing, a lumen, etc.) configured to receive the distal force when some portion of the structure mechanically communicates with (e.g., contacts) the stylet. In examples, leadlet 114 includes a lumen (e.g., an inner lumen) defining one or more features extending from an inner surface of the lumen, each feature configured to receive a distal force. In such examples, the lumen may be configured such that a stylet may be inserted into the lumen of leadlet 114 and exert a distal force on the feature.

In some examples, the stylet may extend alongside IMD 102 and/or leadlet 114 and directly mechanically communicate with (e.g., connect to, be mechanically coupled to, etc.) second electrode 112. In some examples, leadlet 114 may include a casing extending from leadlet 114. The casing may be configured to receive the stylet and be configured to receive a distal force. The casing may be configured to receive the stylet, and the stylet may be configured to mechanically communicate with the casing. The casing may be configured to allow the stylet to connect to second electrode 112. In some examples, the casing may define an enclosure in which second electrode 112 is mechanically supported.

In examples, leadlet 114 defines a leadlet axis from the proximal end of leadlet 114 to the distal end of leadlet 114. The leadlet axis may be substantially linear, curved, and/or curvilinear. Leadlet 114 may be configured to exhibit a bending moment about the leadlet axis as well as transmit an axial force (e.g., to IMD 102) as leadlet 114 accommodates any curvatures necessary to implant into the tissue. The curvature that leadlet 114 exhibits may, at least in part, be due to the force applied by the stylet. For example, the curvature of leadlet 114 may be substantially similar to the shape of the stylet when the stylet is in mechanical communication with leadlet 114.

Figure 2:
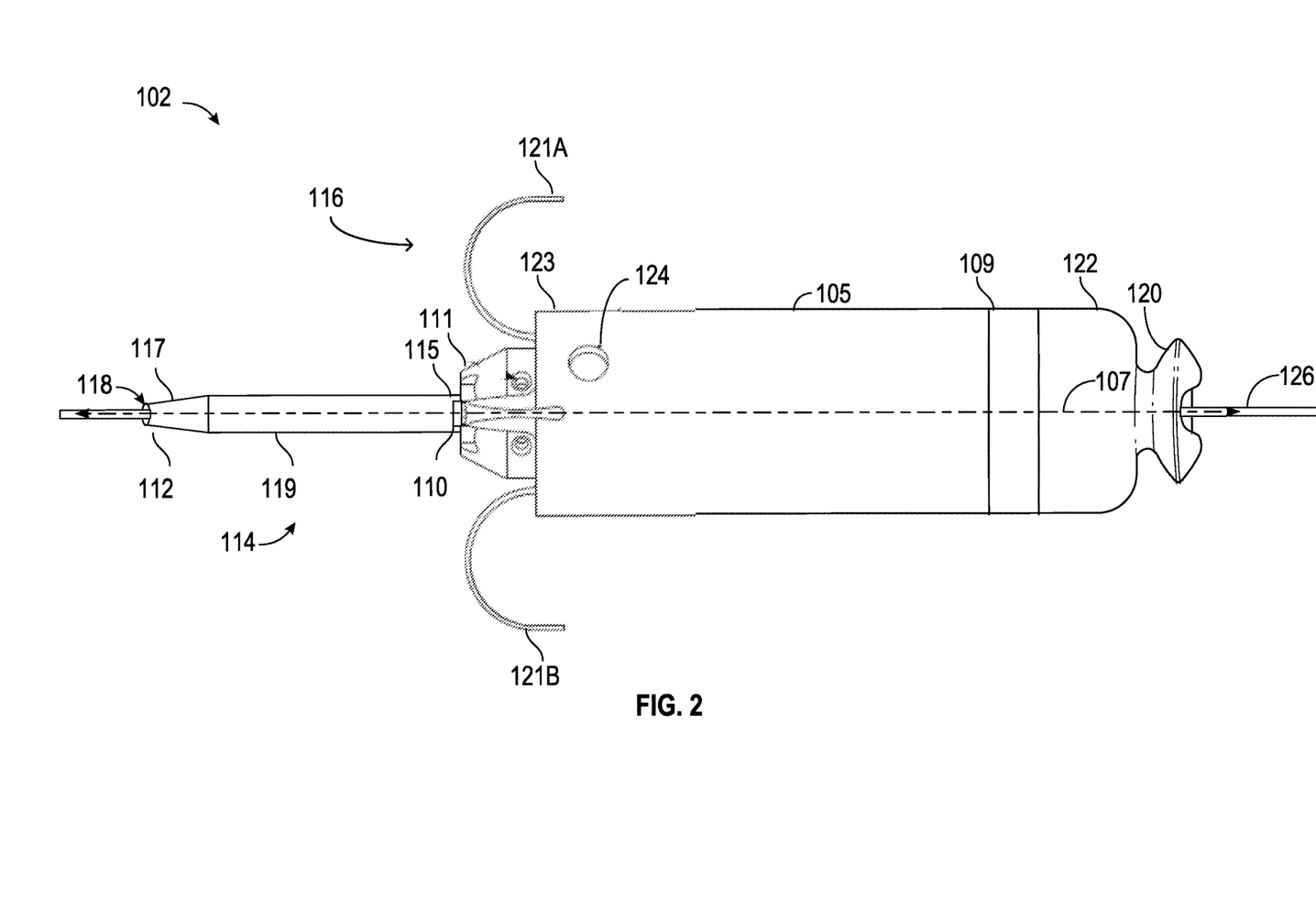
FIG. 2 is a conceptual diagram illustrating an example implantable medical device and stylet according to aspects of this disclosure.

FIG. 2 is a conceptual diagram illustrating IMD 102 and leadlet 114. IMD 102 includes housing 105 extending along longitudinal axis 107 from a proximal end 122 of housing 105 ("housing proximal end 122") to a distal end 123 of housing 105 ("housing distal end 123"). In examples, housing 105 mechanically supports electronic circuitry of IMD 102, such as one or more of sensing circuitry (e.g., for sensing cardiac signals), therapy delivery circuitry (e.g., for generating cardiac pacing pulses), and processing circuitry for controlling the functionality of IMD 102. In examples, housing 105 mechanically supports a return electrode 109. In examples, housing 105 includes a nonconductive coating and defines return electrode 109 as an uncoated portion of housing 105. In any case, return electrode 109 may be operably coupled (e.g., in electrical communication with) the electronic circuitry of IMD 102. Housing 105 may be formed from a biocompatible and biostable metal such as titanium. In some examples, housing 105 may include a hermetically sealed housing. IMD 102 may include any suitable dimensions sufficient to allow IMD 102 to position within heart 106 (e.g., within the RA atrium of heart 106 (FIG. 1)). In some examples, an outer diameter of IMD 102 (e.g., outer diameter of housing 105) may be between about 10 French (Fr) and about 23 Fr, such as about 20 Fr, although other outer diameters of IMD 102 are contemplated.

As shown in FIG. 2, IMD 102 includes first electrode 110 on a distal end 111 of IMD 102 ("IMD distal end 111"). First electrode 110 may be electrically connected to circuitry (e.g., therapy delivery circuitry) within an enclosure defined by housing 105 of IMD 102. First electrode 110 may be configured to receive stimulation signals from IMD 102 for delivery to tissues of a heart, such as a first chamber of heart 106. In examples, first electrode 110 may be configured to allow IMD 102 to sense electrical signals from the first chamber of heart 106.

First electrode 110 may be a shallow electrode configured for sensing and delivery of therapy signals to tissue in a substantially non-invasive manner. For example, first electrode 110 may be configured to provide stimulation to surface tissue (e.g., atrial tissue) in an atrium of heart 106 when tines 116 affix IMD distal end 103 to heart 106.

IMD 102 also includes a second electrode 112 carried by a leadlet 114. Second electrode 112 may be electrically connected to circuitry within housing 105 of IMD 102. Second electrode 112 may be configured to receive stimulation signals from IMD 102 for delivery to tissues of the heart, such as ventricular tissue of heart 106, and may be configured to allow IMD 102 to sense electrical signals from the ventricular tissue of heart 106. First electrode 110 may be a shallow electrode configured for sensing and delivery of therapy signals to tissue in a substantially non-invasive manner. Second electrode 112 may be a deep electrode configured to penetrate the tissues for sensing and delivery of therapy signals.

In general, electrodes (e.g., first electrode 110, second electrode 112, etc.) of IMD 102 may be segmented electrodes, ring electrodes, or any other type of electrode configured to sense electrical signals from and deliver therapy signals to heart 106. In examples, first electrode 110 may be a single electrode disposed at IMD distal end 103, and second electrode 112 may be a single electrode disposed at leadlet distal end 117.

In other examples, first electrode 110 and second electrode 112 may each include a plurality of electrodes arranged in a particular manner on IMD distal end 103 and the leadlet distal end 117, respectively. For example, electrodes may be disposed along leadlet body 119. That is, electrodes may be disposed along a longitudinal axis (e.g., 106) of leadlet 114.

A proximal end 115 of leadlet 114 ("leadlet proximal end 115") is attached to IMD distal end 111. A distal end 117 of leadlet 114 ("leadlet distal end 117") opposite leadlet proximal end 115 may be configured to penetrate tissues (e.g., atrial tissue) of heart 106. In examples, leadlet distal end 117 includes a tip (not shown) configured to penetrate the tissue to form a puncture sized to allow leadlet 114 to be inserted therethrough. In some examples, second electrode 112 is a deep electrode on the tip of leadlet distal end 117 configured to penetrate the tissue to form the puncture sized to allow leadlet 114 to be inserted therethrough.

Leadlet body 119 (or, in other words, the portion of leadlet 114 between leadlet proximal end 115 and leadlet distal end 117) may be configured to stiffen (e.g., during implantation of distal end 117 of leadlet 114 into tissues of the heart). That is, leadlet body 119 may be configured such that leadlet body 119 exhibits substantially no bending moment about some portion of the leadlet axis when leadlet distal end 117 experiences a distal force tending to cause leadlet distal end to insert into tissue. As a result, a user (e.g., a clinician) may more advantageously apply a distal force to leadlet distal end 117, facilitating implantation of second electrode 112 into ventricular tissue of heart 106.

First electrode 110 may be configured to sense and deliver therapy signals to surface tissue in an atrium of heart 106 while second electrode 112 senses and delivers therapy signals within ventricular tissue, enabling the delivery of dual chamber pacing. In examples, leadlet distal end 117 includes a fixation structure (e.g., barbs) configured to resist motion of second electrode 112 in a proximal direction and/or distal direction when leadlet distal end 117 is implanted in the tissues of the heart 106. For example, the fixation structure may be configured to resist a translation of leadlet distal end 117 in a proximal direction when leadlet distal end 117 is implanted in the tissues of heart 106. In examples, the fixation structure is configured such that, when distal end 117 is implanted within tissue, the fixation structure causes leadlet 114 to exert a first reaction force (in a proximal direction) when a distally directed force is exerted on leadlet distal end 117, and exert a second reaction force (in a distal direction) when a proximally directed force is exerted on leadlet distal end 117. In such examples, the magnitude of the first reaction force may be less than or equal to the magnitude of the distally directed force (allowing movement of leadlet 114 in a distal direction), and the magnitude of the second reaction force may be equal to or greater than the magnitude of the proximally directed force (resisting movement of leadlet 114 in a proximal direction). Hence, when leadlet distal end 117 is implanted within tissue and fixation device 116 attaches to tissues of heart 106, leadlet 114 may be substantially anchored at leadlet proximal end 115 and leadlet distal end 117. Leadlet body 119 may be configured to flex between the substantially anchored lead proximal end 115 and leadlet distal end 117, such that leadlet 114 may accommodate movements of heart 106 while allowing IMD 102 and leadlet 114 to remain in an implanted position within the patient. The fixation structure may be configured such that second reaction force is overcome with a proximally directed force of sufficient magnitude, such as a proximally directed force on leadlet distal end 117 caused by a clinician.

Leadlet 114 may be configured to stiffen such that leadlet 114 more effectively penetrates the tissue, facilitating implantation of leadlet 114. For example, leadlet 114 may define a lumen 118 configured to receive a stylet 126, such that stylet 126 may be inserted into lumen 118. Leadlet 114 may be configured such that a distal force imparted on stylet 126 results in a distal force on leadlet 114. Leadlet 114 may define a bearing structure (e.g., lumen 118, or another structure) configured to receive the distal force when some portion of the bearing structure mechanically communicates with (e.g., contacts) stylet 126. The bearing structure may be configured to transfer at least some portion of the distal force to leadlet distal end 117. Leadlet 114 may be configured such that a distal force exerted by stylet 126 on leadlet 114 causes leadlet distal end 117 to insert into the tissue of heart 106 (FIG. 1). Leadlet 114 may be configured to receive the distal force from the distal end of stylet 126. In some examples, leadlet 114 may be configured to simultaneously maintain mechanical communication with stylet 126 and allow stylet 126 to extend beyond leadlet distal end 117.

In some examples, leadlet 114 may be configured to vary in stiffness during implantation of leadlet 114 based on which portion of the bearing structure (e.g., lumen 118, or another structure) of leadlet 114 receives the distal force. For example, lumen 118 of leadlet 114 may include multiple features (not shown), with which stylet 126 may mechanically communicate, extending from the inner surface of lumen 118 at various locations along an axial length of leadlet 114. A user (e.g., a clinician) may insert stylet 126 into lumen 118 of leadlet 114 such that stylet 126 contacts a feature at or near leadlet distal end 117. In this way, stylet 126 may reinforce leadlet body 119 between leadlet proximal end 115 and leadlet distal end 117, stiffening the length of leadlet body 119 between leadlet proximal end 115 and leadlet distal end 117. Similarly, the user may insert stylet 126 into lumen 118 of leadlet 114 such that stylet 126 contacts a feature at or near the middle portion of leadlet 114, thus stiffening the length of leadlet body 119 between proximal end 115 and the middle portion of leadlet 114. In examples, leadlet body 119 has a length of from about 6 millimeters (mm) to about 20 mm, though other lengths are contemplated.

In examples, leadlet 114 is configured to exhibit a first stiffness when stylet 126 exerts a distal force on the bearing structure and a second stiffness in the absence of a distal force exerted by stylet 126 on the bearing structure. The first stiffness may be greater than the second stiffness. The stiffness may refer to an ability of leadlet 114 to resist bending and/or flexing about longitudinal axis 107 when an external force or moment is applied to leadlet 114. For example, leadlet 114 may be configured such that, when leadlet 114 experiences a torque on leadlet 114 around leadlet proximal end 115, leadlet 114 defines a first curvature having a first radius when stylet 126 mechanically communicates with leadlet 114 (e.g., via the bearing structure). Further, leadlet 114 may be configured such that, when leadlet 114 experiences the torque on leadlet 114 around leadlet proximal end 115, leadlet 114 defines a second curvature having a second radius in the absence of any mechanical communication with stylet 126, where the first radius of curvature is greater than the second radius of curvature (such that the first curvature is less than the second curvature). In some examples, leadlet 114 is configured to receive some portion of stylet 126, and leadlet 114 is configured to exhibit the first stiffness when leadlet 114 receives stylet 126 and exhibit the second stiffness when stylet 126 is displaced (e.g., separated from) leadlet 114.

As shown in FIG. 2, IMD 102 may define a lumen access opening to lumen 118. In examples, IMD 102 defines the lumen access at a leadlet distal end 117. IMD 102 may define lumen 118 such that stylet 126 may extend through the lumen access beyond leadlet distal end 117. After leadlet 114 is implanted into target implant site 104, stylet 126 may be removed (e.g., partially or entirely) from lumen 118 of leadlet 114. Leadlet 114 may be configured such that leadlet body 119 may flex following removal of stylet 126. In examples, leadlet 114 is configured such that stylet 126 may be inserted into an opening located on proximal end 122 of IMD 102 (or another portion of IMD 102, such as a housing wall of IMD 102). Leadlet 114 may be configured to allow stylet 126 to translate within a passage extending from the opening (e.g., located on proximal end 122, housing wall of IMD 102, etc.) to distal end 117 of leadlet 114 to mechanically communicate with leadlet 114. In other examples, leadlet 114 may include a casing extending from an outer surface of leadlet 114 configured to accommodate stylet 126 and/or enable stylet 126 to connect to second electrode 112. Like lumen 118, the casing may be configured to allow leadlet 114 to flex and, when in mechanical communication with stylet 126 (or another elongate member, be configured to stiffen leadlet 114. Leadlet 114 may be configured to exhibit the first stiffness when stylet 126 extends through lumen 118 or the passage and exhibit the second stiffness when stylet 126 is removed from lumen 118 or the passage. In some examples, stylet 126 may extend alongside IMD 102 and/or leadlet 114 and directly mechanically communicate with (e.g., connect to, be mechanically coupled to, etc.) second electrode 112.

As described above, IMD 102 may include fixation device 116 configured to engage tissue. In examples, and shown in FIG. 2, fixation device 116 may include one or more fixation tines, such as tine 121A and/or tine 121B (collectively, "tines 121"), configured to engage tissue. However, other examples of fixation device 116 are contemplated by this disclosure, including fixation devices with a different number of tines (e.g., one, four, eight, etc.), a different arrangement of tines (e.g., about longitudinal axis 107 of IMD 102), different types of tines (e.g., helically-shaped fixation tines), and/or the like.

Fixation device 116 may be configured to substantially maintain contact between IMD 102 and the tissue at a target implant site (e.g., target implant site 104 (FIG. 1)). Fixation device 116 may be configured to substantially maintain contact between housing distal end 123 and the tissue. Any of tines 121 may be a deep tine, a shallow tine, and/or the like. Any of tines 121 may have elastic or superelastic properties, and may, in some cases, be configured to pierce and potentially penetrate into or through the tissue.

Fixation device 116 may include one or more sections, such as an elastically deformable material preset into one or more curved sections and one or more optional substantially straight sections. Fixation device 116 may be formed to have a preset shape and may be superelastic, e.g., made of the nickel-titanium alloy Nitinol. In examples, fixation device 116 defines a ribbon shape configured to deform along a plane normal to longitudinal axis 107 and resist twisting outside of the plane. In some examples, fixation device 116 may include two or more curved sections (e.g., knuckles). For example, fixation device 116 may include a base in proximity to housing distal end 123 and a plurality of tines (e.g., tine 121A, a tine 121B, etc.) fixedly attached and spaced from one another around a perimeter of housing distal end 123.

Fixation device 116 may include a proximal portion and a distal portion. The proximal portion may include a proximal section fixedly attached to the base in proximity to the housing distal end 123 and extending from the base in a first direction. The first curved section may define a first deformable pre-formed curvature and extend from the proximal section laterally, outward from longitudinal axis 107. A first straight section of fixation device 116 may extend from the first curved section laterally, outward from longitudinal axis 107 in a second direction. A second curved section may define a second deformable pre-formed curvature and extend from the first straight section laterally, outward from longitudinal axis 107. The distal portion of fixation device 116 may include a second straight section extending from the second curved section in a third direction oriented generally opposite the first direction. A third curved section may define a third deformable pre-formed curvature and extend from the second straight section. A tip section may extend from the third curved section toward longitudinal axis 107 and terminating in a free distal end.

Fixation device 116 may be configured to have a target deflection stiffness and a target deployment stiffness. The target deflection stiffness may include a measure of a resistance to force applied to IMD 102 in a proximal direction when fixation device 116 is engaged with tissue at target implant site 104. In some examples, the target deflection stiffness may be selected to enable fixation device 116 to deflect a predetermined amount to enable visualization of fixation device 116 under fluoroscopy. In examples, the target deflection stiffness may be within a range from about 0.2 N to about 0.8 N, such as about 0.3 N to about 0.6 N. The deployment stiffness may include a measure of a force applied by fixation device 116 as fixation device 116 moves from a deformed configuration to an undeformed configuration upon deployment of IMD 102 from the distal opening of delivery catheter 108 such that the distal end of fixation device 116 penetrates the atrial or ventricular myocardium. In examples, the target deployment stiffness may be within a range from about 0.6 N to about 1.2 N.

In examples, IMD 102 includes a retrieval structure 120 fixedly attached to or formed integrally with housing proximal end 122. Retrieval structure 120 may be configured for temporarily tethering IMD 102 to a delivery catheter or a retrieval catheter, such as delivery catheter 108. Retrieval structure 120 may be configured to couple to tether assemblies. A tether assembly may include a tether head assembly, a tether handle assembly, and a pull wire. The tether head assembly may be attached to the pull wire and configured to releasably retain an attachment member of a medical device (e.g., an intracardiac device). In examples, a tether handle assembly is configured to retain the pull wire attached to the tether head assembly.

IMD 102 may include a marker 124, which in some examples may be a radiopaque marker. Marker 124 may be visible via medical imaging such as fluoroscopy and allow a clinician to view and adjust the rotational orientation of IMD 102 to achieve a desired trajectory and/or a desired advancement path of tines 121 to target implant site 104.

Figure 3:
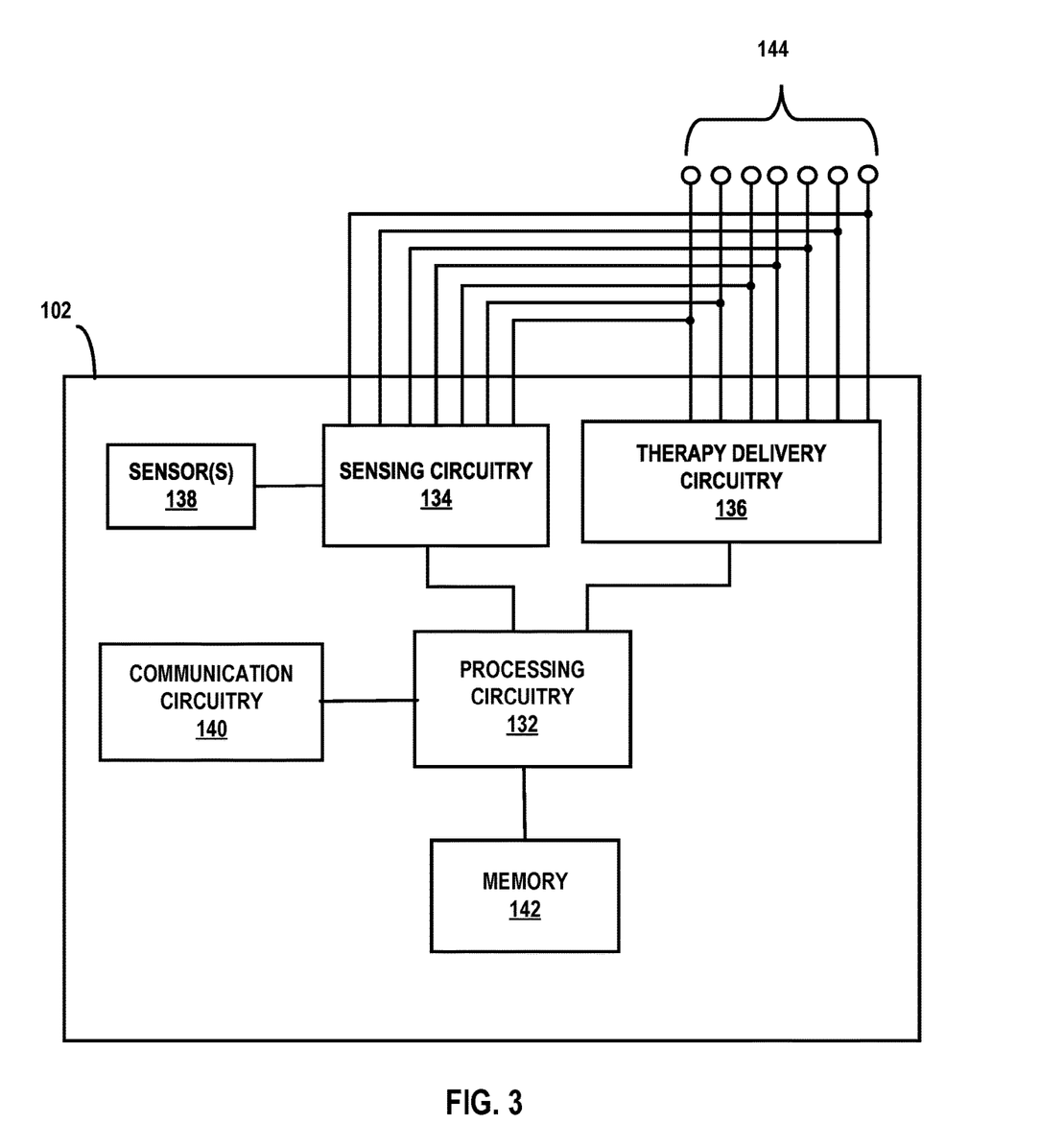
FIG. 3 is a block diagram illustrating circuitry of an example implantable medical device.

FIG. 3 is a functional block diagram illustrating an example configuration of IMD 102. As shown in FIG. 3, IMD 102 includes processing circuitry 132, sensing circuitry 134, therapy delivery circuitry 136, sensors 138, communication circuitry 140, and memory 142. Processing circuitry 132, sensing circuitry 134, therapy delivery circuitry 136, and/or communication circuitry 140 may be examples of circuitry 113, In some examples, memory 142 includes computer-readable instructions that, when executed by processing circuitry 132, cause IMD 102 and processing circuitry 132 to perform various functions attributed to IMD 102 and processing circuitry 132 herein. Memory 142 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 132 may include fixed function circuitry and/or programmable processing circuitry. Processing circuitry 132 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 132 may include multiple components, such as any combination of one or more microprocessors, one or more controllers, one or more DSPs, one or more ASICs, or one or more FPGAs, as well as other discrete or integrated logic circuitry. The functions attributed to processing circuitry 132 herein may be embodied as software, firmware, hardware or any combination thereof.

In some examples, processing circuitry 132 may receive (e.g., from an external device), via communication circuitry 140, a respective value for each of a plurality of cardiac sensing parameters, cardiac therapy parameters (e.g., cardiac pacing parameters), and/or electrode vectors. Processing circuitry 132 may store such parameters and/or electrode vectors in memory 142.

Therapy delivery circuitry 136 and sensing circuitry 134 are electrically coupled to electrodes 144, which may correspond to first electrode 110, second electrode 112, return electrode 109, and/or other electrodes of medical system 100. Processing circuitry 132 is configured to control therapy delivery circuitry 136 to generate and deliver electrical therapy to heart 106 via electrodes 144. Electrical therapy may include, for example, pacing pulses, or any other suitable electrical stimulation. Processing circuitry 132 may control therapy delivery circuitry 136 to deliver electrical stimulation therapy via electrodes 144 according to one or more therapy parameter values, which may be stored in memory 142. Therapy delivery circuitry 136 may include capacitors, current sources, and/or regulators, in some examples.

In addition, processing circuitry 132 is configured to control sensing circuitry 134 to monitor signals from electrodes 144 in order to monitor electrical activity of heart 106. Sensing circuitry 134 may include circuits that acquire electrical signals, such as filters, amplifiers, and analog-to-digital circuitry. Electrical signals acquired by sensing circuitry 134 may include intrinsic and/or paced cardiac electrical activity, such as atrial depolarizations and/or ventricular depolarizations. Sensing circuitry 134 may filter, amplify, and digitize the acquired electrical signals to generate raw digital data. Processing circuitry 132 may receive the digitized data generated by sensing circuitry 134. In some examples, processing circuitry 132 may perform various digital signal processing operations on the raw data, such as digital filtering. In some examples, in addition to sensing circuitry 134, IMD 102 optionally may include sensors 138, which may be one or more pressure sensors and/or one or more accelerometers, as examples. Communication circuitry 140 may include any suitable hardware (e.g., an antenna), firmware, software, or any combination thereof for communicating with another device, e.g., external to the patient.

Figure 4:
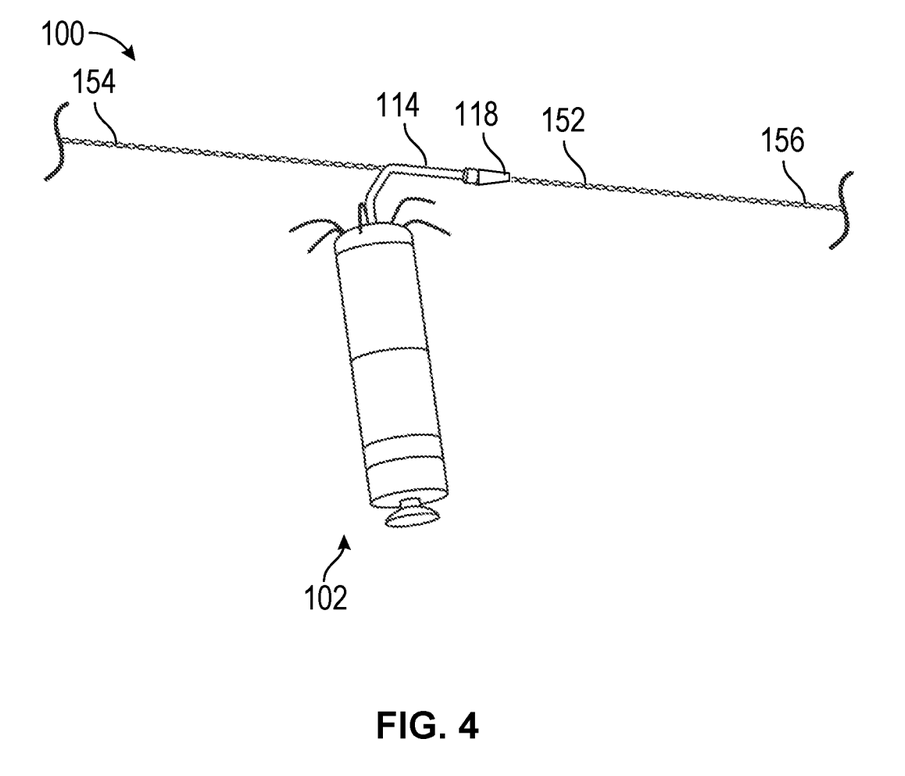
FIG. 4 is a conceptual diagram illustrating an example medical system including an implantable medical device and a guidewire according to aspects of this disclosure.

FIG. 4 is a conceptual diagram illustrating medical system 100 of FIG. 1, including implantable medical device 102 and a guidewire 152. In examples, guidewire 152 has a proximal portion 154 and a distal portion 156. Distal portion 156 may include a distal end (not shown in FIG. 4) configured to penetrate a septal boundary of heart 106. Proximal portion 154 may include a proximal end (not shown in FIG. 4) that in turn includes a user device (e.g., a trigger) configured to cause distal portion 156 to expand when the septal boundary separates proximal portion 154 and distal portion 156. A lumen 118 of leadlet 114 may be configured to receive guidewire 152 such that leadlet 114 may translate over guidewire 152 toward a target implant site 104. IMD 102 may be delivered to the tissue by translating over guidewire 152.

For example, a clinician may place guidewire 152 across the septum (e.g., from the RA, right ventricle (RV), etc.) into the LV chamber near or through the LBB. IMD 102 may then be translated over the guidewire until IMD 102 is delivered to target implant site 104. When the septal boundary separates proximal portion 154 and distal portion 156 of guidewire 152, the clinician may use the user device to cause distal portion 156 to expand, resisting movement of guidewire 152 in the proximal direction. Guidewire 152 may include a tip configured to penetrate the tissue to form a puncture sized to allow leadlet 114 to be inserted therethrough.

In examples, guidewire 152 may be removed from target implant site 104 after delivery and implantation of IMD 102. In other examples, guidewire 152 is configured to be removed before IMD 102 is implanted into the tissue. For example, guidewire 152 may be removed before IMD 102 reaches the LV endocardium, reducing the probability that IMD 102 exceeds a desired penetration depth of the tissue.

Guidewire 152 may be placed using a plurality of fluoroscope angles. In examples, guidewire 152 is placed by affixing (e.g., using a helically-shaped fixation tine) a pacing catheter into the target implant site 104 and inserting the guidewire into the pacing catheter by using one of the plurality of fluoroscope angles. The guidewire may be inserted into a delivery catheter (e.g., delivery catheter 108) configured to indicate (e.g., via tactile feedback) when the delivery catheter, and thus guidewire 152, and pacing catheter are properly aligned.

Figure 5:
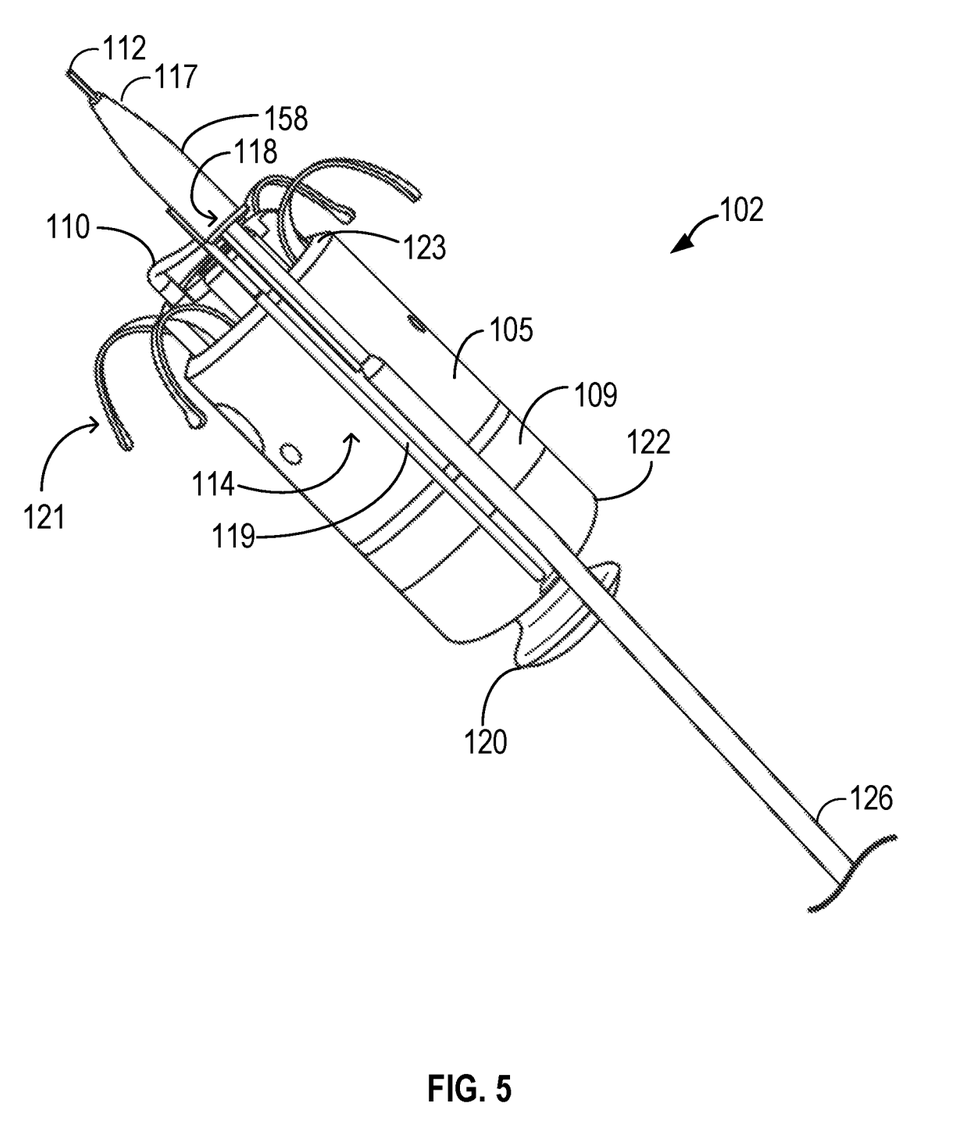
FIG. 5 is a conceptual diagram illustrating an example implantable medical device and stylet according to aspects of this disclosure.

FIG. 5 is a conceptual diagram illustrating an IMD 202 and a leadlet 214. IMD 202 may be substantially similar to IMD 102 except for any differences described herein. Leadlet 214 may be substantially similar to IMD 102, except for any differences described herein. As shown in FIG. 5, IMD 202 may define a proximal portion 258 ("IMD proximal portion 258") and a distal portion 260 ("IMD distal portion 260"). Leadlet 214 may extend from IMD distal portion 260, such as a side of a distal end of IMD 202.

Figure 6:
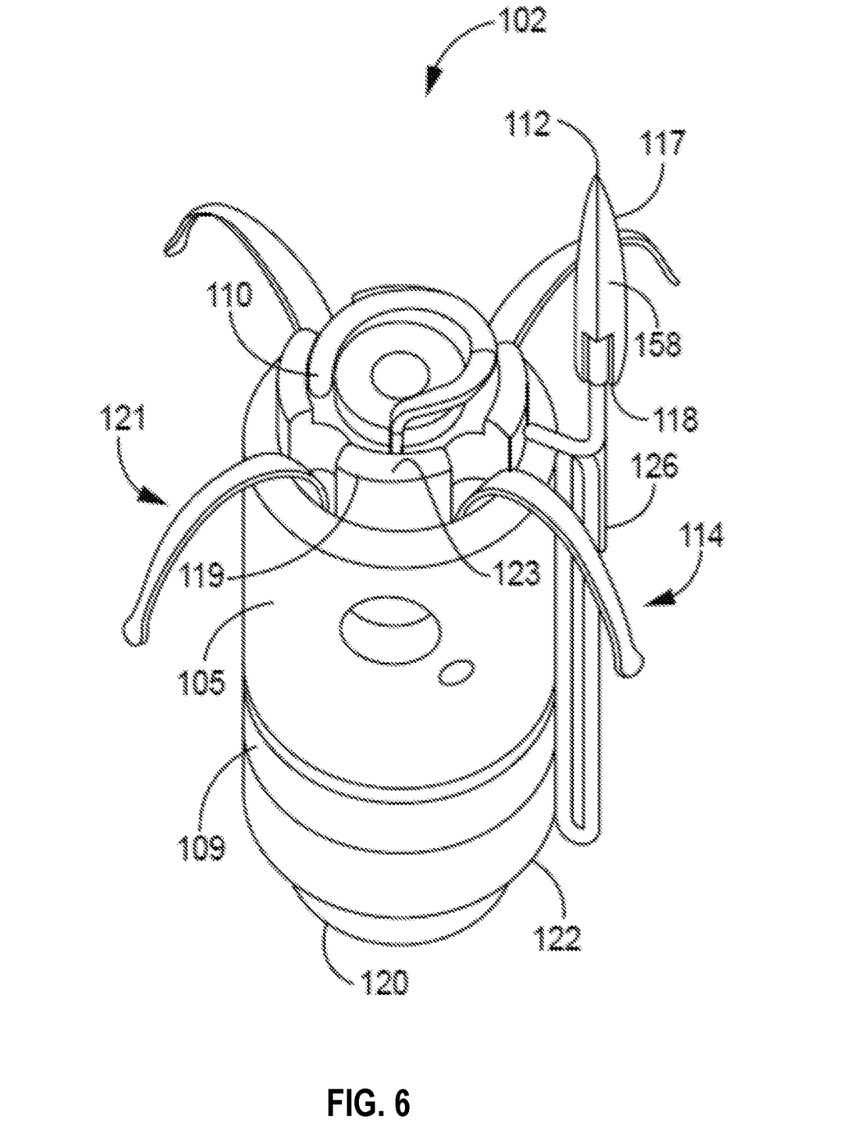
FIG. 6 is a conceptual diagram of the implantable medical device of FIG. 5 illustrating a leadlet, a casing, and a stylet according to aspects of this disclosure.

FIG. 5 and FIG. 6 is a conceptual diagram illustrating IMD 102 with leadlet 114 including a casing 158 configured to receive a distal force from stylet 126. Leadlet 114 defines an inner lumen 118 within casing 158 configured to receive stylet 126. Lumen 118 defines one of more structures configured to mechanically communicates with the stylet 126 when lumen 118 receives stylet 126. Casing 158 is configured to transmit at least some portion of the distal force from stylet 126 to second electrode 112 to cause, for example, penetration of second electrode 112 into tissue. In this way, a user, such as a clinician, may impart a distal force on a distal end 217 of leadlet 214 ("leadlet distal end 217") causing leadlet distal end 217 to penetrate the ventricular tissue.

As illustrated in FIG. 5 and FIG. 6, leadlet 114 may be configured to extend from a side of housing 105. In examples, leadlet 114 is configured to fold and/or bend into a relatively compact shape, such that medical system 100 may be transferred to the vicinity of target implant site 104 (FIG. 1) within a section (e.g., a cup section) of catheter 108 (FIG. 1). Leadlet 114 may be configured to fold and/or bend such that IMD 102 and leadlet 114 define a cross-section fitting within a cross-sectional dimension defined by catheter 108. In examples, leadlet 114 is configured to fold and/or bend to accommodate stylet 126 within catheter 108. For example, IMD 102 and leadlet 114 may be configured such that IMD 102, leadlet 114, and stylet 126 define a cross-section fitting within the cross-sectional dimension defined by catheter 108. In examples, IMD 102 and leadlet 114 are configured to define the cross-section fitting within the cross-sectional dimension defined by catheter 108 when casing 158 receives stylet 126, such that catheter 108 may transferred IMD 102, leadlet 114, and stylet 126 to the vicinity of target implant site 104.

Figure 7:
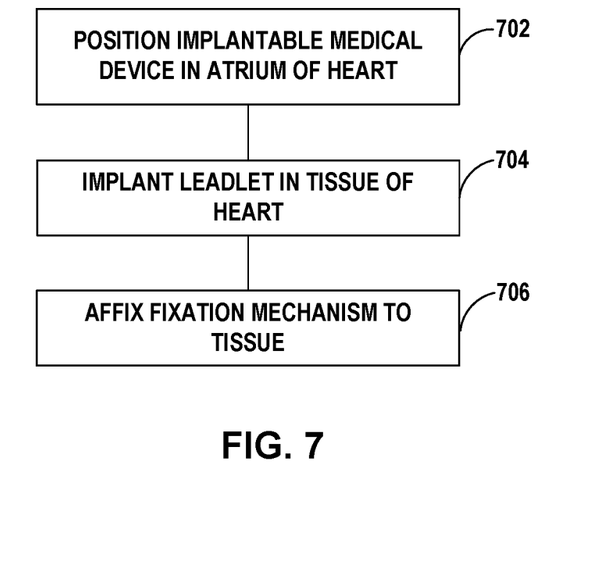
FIG. 7 is a flow diagram of an example technique for positioning a medical system within a heart.

A technique for positioning a medical system 100 within heart 106 is illustrated in FIG. 7. The technique includes positioning IMD 102 of medical system 100 within heart 106 (e.g., an atrium) by transmitting a distal force to IMD 102 (702). The technique may include inserting IMD 102 into the delivery catheter lumen of delivery catheter 108 and using stylet 126 to exert a distal force on leadlet distal end 117 to translate leadlet 114, and thus IMD 102, through delivery catheter 108.

The technique includes implanting leadlet 114 in tissues (e.g., ventricular tissue) of heart 106 (704). Leadlet 114 may be configured to vary in stiffness (in order to flex or be rigid) to facilitate implantation of leadlet 114 into tissue. For example, leadlet 114 may receive stylet 126 or another elongate member that is configured to exert a distal force on leadlet 114 to cause leadlet distal end 117 to implant into tissue. In this way, first electrode 110 may contact surface tissue of the atrium of heart 106 while second electrode 112 is implanted within tissue of heart 106, such that first electrode 110 may sense and delivery therapy signals to surface tissue in an atrium of heart 106 while second electrode 112 senses and delivers therapy signals within ventricular tissue. This may enable the delivery of dual chamber pacing.

In some examples, during implantation of leadlet 114, at least a portion of leadlet body 119 may stiffen when lumen 118 receives (e.g., partially or entirely) stylet 126. For example, lumen 118 of leadlet 114 may include multiple features, with which stylet 126 may mechanically communicate, extending from the inner surface of lumen 118 at various locations along an axial length of leadlet 114. A user (e.g., a clinician) may insert stylet 126 into lumen 118 of leadlet 114 such that stylet 126 contacts a feature at or near leadlet distal end 117. In this way, stylet 126 may stiffen the length of leadlet body 119 between leadlet proximal end 115 and leadlet distal end 117. Similarly, the user may insert stylet 126 into lumen 118 of leadlet 114 such that stylet 126 contacts a feature at or near the middle portion of leadlet 114, thus stiffening the length of leadlet body 119 between proximal end 115 and the middle portion of leadlet 114.

In examples, the technique includes affixing fixation device 116 of IMD 102 to tissues of heart 106 (706). The technique may include using stylet 126 to apply a distal force to leadlet 114 until tines 121 of IMD 102 penetrate tissues of heart 106. A clinician may then confirm adequate fixation (e.g., that IMD 102 is secured well enough to maintain an orientation of IMD 102 with respect to target implant site 104 to prevent motion of IMD 102 in a proximal direction) of tines 121. For example, a pull test or a tug test may be performed under fluoroscopy to confirm that tines 121 have engaged the tissue to confirm adequacy of implantation of IMD 102. The pull test or tug test may include the clinician pulling or tugging on IMD 102, e.g., via a tether coupled to a proximal end of IMD 102, and observing movement of tines 121 to determine if tines 121 are engaged in tissue. For example, tines 121 that are embedded in tissue may deflect or bend as IMD 102 is pulled or tugged in the proximal direction.

In some examples, leadlet 114 may be implanted in tissue and then IMD 102 may be affixed to target implant site 104. For example, stylet 126 may exert a distal force to leadlet distal end 117, causing leadlet distal end 117 to penetrate the ventricular tissue. In examples, leadlet 114 may be advanced distally and proximally within the tissue, such that a clinician may evaluate and/or adjust the location of leadlet 114 (e.g., second electrode 112) within the tissue. As such, the clinician may use leadlet 114 to map a prospective implantation site prior to implantation of leadlet 114. The clinician may exert a distal force on some portion of medical system 100 (e.g., IMD 102) to cause tines 121 to engage with tissue and implant IMD 102 to target implant site 104. In examples, the technique includes first implanting leadlet 114 (e.g., at an evaluated implantation location), then exerting the distal force on IMD 102 to cause tines 121 to engage the tissue.

This disclosure includes various examples, such as the following examples.

Example 1: A medical system includes an implantable medical device that carries a first electrode on a distal end of the implantable medical device and a return electrode, wherein the implantable medical device is configured to be positioned within a heart; a leadlet including a proximal end and a distal end, wherein the proximal end is attached to the implantable medical device, wherein the distal end is configured to penetrate tissue of the heart, wherein the leadlet carries a second electrode, and wherein a body of the leadlet between the proximal end and the distal end is configured to flex when the distal end is implanted in the tissue of the heart; and a fixation device attached to the implantable medical device, wherein the fixation device is configured to affix the distal end of the implantable medical device to the heart.

Example 2: The medical system of example 1, wherein the leadlet is configured to flex to define a substantially curvilinear shape.

Example 3: The medical system of example 1 or 2, wherein the tissue of the heart is ventricular tissue, and wherein the first electrode is configured to provide stimulation to surface tissue in an atrium of the heart when the fixation device affixes the distal end of the implantable medical device to the heart.

Example 4: The medical system of any of examples 1-3, wherein the proximal end of the leadlet is attached to the distal end of the implantable medical device.

Example 5: The medical system of any of examples 1-4, wherein the first electrode and the second electrode are electrically connected to therapy delivery circuitry within the implantable medical device.

Example 6: The medical system of any of examples 1-5, wherein the distal end of the leadlet includes a fixation structure configured to resist motion of the second electrode in a proximal direction when the distal end is implanted in the tissues of the heart.

Example 7: The medical system of any of examples 1-6, wherein the body of the leadlet has a length of from about 6 millimeters to about 20 millimeters.

Example 8: The medical system of any of examples 1-7, wherein the leadlet is configured to receive a stylet, and wherein the distal end is configured to move in a distal direction when the leadlet receives the stylet and a distal force is exerted on the stylet.

Example 9: The medical system of any of examples 1-8, wherein the leadlet is configured to receive a stylet, and wherein the body of the leadlet is configured to stiffen when the leadlet receives the stylet.

Example 10: The medical system of any of examples 1-9, further including a stylet configured to control a flexibility of the leadlet by mechanically communicating with one or more features of a lumen of the leadlet.

Example 11: The medical system of example 10, wherein the stylet includes a tip configured to penetrate the tissue to form a puncture sized to allow the leadlet to be inserted therethrough, and wherein the leadlet is configured to allow the stylet to extend beyond the distal end of the leadlet.

Example 12: The medical system of example 10 or 11, wherein the stylet configured to be inserted into a medical device lumen of the medical device and extend from the opening of the medical device toward a distal end of the leadlet.

Example 13: The medical system of any of examples 10-12, wherein the stylet is configured to be inserted into the second electrode or into a casing extending from an outer surface of the leadlet.

Example 14: The medical system of any of examples 1-13, wherein the implantable medical device is configured to remain in an atrium of the heart when fixation device affixes the distal end of the implantable medical device to the heart.

Example 15: The medical system of any of examples 1-14, wherein the leadlet carries the second electrode at the distal end of the leadlet.

Example 16: The medical system of any of examples 1-15, wherein the fixation device is configured to affix the implantable medical device to the tissue by resisting motion of the implantable medical device in a proximal direction.

Example 17: The medical system of any of examples 1-16, wherein the implantable medical device includes a housing, and wherein the fixation device is configured to affix the implantable medical device to the tissue by affixing a distal end of the housing to the tissue.

Example 18: The medical system of any of examples 1-17, wherein the implantable medical device further includes a housing with therapy delivery circuitry housed therein.

Example 19: The medical system of any of examples 1-18, wherein the implantable medical device includes a housing defining the return electrode.

Example 20: The medical system of any of examples 1-19, wherein the implantable medical device carries the first electrode at or near a distal end of the housing.

Example 21: The medical system of any of examples 1-20, wherein the leadlet includes a tip configured to penetrate the tissue when a force in the distal direction is applied to the leadlet to form a puncture through which the leadlet may be inserted.

Example 22: The medical system of any of examples 1-21, wherein the medical device defines a medical device lumen configured to enable the medical device to translate over a guidewire.

Example 23: The medical system of example 22, further including the guidewire, wherein the guidewire includes a proximal portion and a distal portion, wherein the distal portion includes a distal end configured to penetrate a septal boundary, and wherein the proximal portion includes a user device configured to cause the distal portion to expand when the septal boundary separates the proximal portion and the distal portion.

Example 24: The medical system of any of examples 1-23, further including a delivery catheter defining a catheter lumen, wherein the delivery catheter defines a lumen opening to the catheter lumen at a distal end of the delivery catheter, and wherein the catheter lumen and the lumen opening are sized to allow the medical device to translate through the catheter lumen and through the lumen opening.

Example 25: A method of implanting a medical system includes positioning an implantable medical device within a heart, wherein the implantable medical device carries a first electrode and a return electrode; implanting a leadlet, extending from the implantable medical device, in a tissue of the heart, wherein the leadlet carries a second electrode, wherein the leadlet is configured to flex while implanted in the tissue of the heart, and wherein a distal end of the leadlet is configured to penetrate the tissue; and affixing a fixation device, attached to the implantable medical device, to the tissue.

Example 26: The method of example 25, wherein the leadlet is configured to flex to define a substantially curvilinear shape.

Example 27: The method of example 25 or 26, wherein the tissue of the heart is ventricular tissue, and wherein the first electrode is configured to provide stimulation to surface tissue in an atrium of the heart when the fixation device affixes the distal end of the implantable medical device to the heart.

Example 28: The method of any of examples 25-27, wherein the proximal end of the leadlet is attached to the distal end of the implantable medical device.

Example 29: The method of any of examples 25-28, wherein the first electrode and the second electrode are electrically connected to therapy delivery circuitry within the implantable medical device.

Example 30: The method of any of examples 25-29, wherein the distal end of the leadlet includes a fixation structure configured to resist motion of the second electrode in a proximal direction when the distal end is implanted in the tissues of the heart.

Example 31: The method of any of examples 25-30, wherein the body of the leadlet has a length of from about 6 millimeters to about 20 millimeters.

Example 32: The method of any of examples 25-31, wherein the leadlet is configured to receive a stylet, and wherein the distal end is configured to move in a distal direction when the leadlet receives the stylet and a distal force is exerted on the stylet.

Example 33: The method of any of examples 25-32, wherein the leadlet is configured to receive a stylet, and wherein the body of the leadlet is configured to stiffen when the leadlet receives the stylet.

Example 34: The method of any of examples 25-33, further including a stylet configured to control a flexibility of the leadlet by mechanically communicating with one or more features of a lumen of the leadlet.

Example 35: The method of example 34, wherein the stylet includes a tip configured to penetrate the tissue to form a puncture sized to allow the leadlet to be inserted therethrough, and wherein the leadlet is configured to allow the stylet to extend beyond the distal end of the leadlet.

Example 36: The method of example 34 or 35, wherein the stylet is inserted into a medical device lumen of the medical device and extends from the opening of the medical device toward a distal end of the leadlet.

Example 37: The method of any of examples 34-36, wherein the stylet is inserted into the second electrode or a casing extending from an outer surface of the leadlet.

Example 38: The method of any of examples 25-37, wherein the implantable medical device is configured to remain in an atrium of the heart when fixation device affixes the distal end of the implantable medical device to the heart.

Example 39: The method of any of examples 25-38, wherein the leadlet carries the second electrode at the distal end of the leadlet.

Example 40: The method of any of examples 25-39, wherein the fixation device is configured to affix the implantable medical device to the tissue by resisting motion of the implantable medical device in a proximal direction.

Example 41: The method of any of examples 25-40, wherein the implantable medical device includes a housing, and wherein the fixation device is configured to affix the implantable medical device to the tissue by affixing a distal end of the housing to the tissue.

Example 42: The method of any of examples 25-41, wherein the implantable medical device further includes a housing with therapy delivery circuitry housed therein.

Example 43: The method of any of examples 25-42, wherein the implantable medical device includes a housing defining the return electrode.

Example 44: The method of any of examples 25-43, wherein the implantable medical device carries the first electrode at or near a distal end of the housing.

Example 45: The method of any of examples 25-44, wherein the leadlet includes a tip configured to penetrate the tissue when a force in the distal direction is applied to the leadlet to form a puncture sized to allow the leadlet to be inserted therethrough.

Example 46: The method of any of examples 25-45, wherein the medical device defines a medical device lumen configured to enable the medical device to translate over a guidewire.

Example 47: The method of example 46, further including the guidewire, wherein the guidewire includes a proximal portion and a distal portion, wherein the distal portion includes a distal end configured to penetrate a septal boundary, and wherein the proximal portion includes a user device configured to cause the distal portion to expand when the septal boundary separates the proximal portion and the distal portion.

Various examples of the disclosure have been described. Any combination of the described systems, operations, or functions is contemplated. These and other examples are within the scope of the following claims.

What is claimed is:

1. A medical system comprising:
    an implantable medical device that carries a first electrode on a distal end of the implantable medical device and a return electrode, wherein the implantable medical device is configured to be positioned within a heart;
    a leadlet including a proximal end and a distal end, wherein the proximal end is attached to the implantable medical device, wherein the distal end is configured to penetrate tissue of the heart, wherein the leadlet carries a second electrode, and wherein a body of the leadlet between the proximal end and the distal end is configured to flex when the distal end is implanted in the tissue of the heart,
    wherein the leadlet includes a bearing structure configured to receive an elongate member, and wherein the distal end of the leadlet is configured to move in a distal direction when the bearing structure receives the elongate member and a distal force is exerted on the elongate member; and
    a fixation device attached to the implantable medical device, wherein the fixation device is configured to affix the implantable medical device to the heart.

2. The medical system of claim 1, wherein the leadlet is configured to flex to define a substantially curvilinear shape when the fixation device is affixed to the heart and the distal end is implanted in the tissue of the heart.

3. The medical system of claim 1, wherein the tissue of the heart is ventricular tissue, and wherein the first electrode is configured to provide stimulation to surface tissue in an atrium of the heart when the fixation device affixes the distal end of the implantable medical device to the heart.

4. The medical system of claim 1, wherein the first electrode and the second electrode are electrically connected to circuitry within the implantable medical device, wherein the circuitry is configured to deliver stimulation signals to the heart using at least one of the first electrode or the second electrode.

5. The medical system of claim 1, wherein the first electrode and the second electrode are electrically connected to circuitry within the implantable medical device, wherein the circuitry is configured to sense signals from the heart using at least one of the first electrode or the second electrode.

6. The medical system of claim 1, further comprising a fixation structure supported by the leadlet, wherein the fixation structure is configured to resist motion of the second electrode in a proximal direction when the distal end is implanted in the tissues of the heart.

7. The medical system of claim 1, wherein the leadlet is configured to exhibit a first stiffness when the bearing structure receives the elongate member and a second stiffness when the elongate member is displaced from the bearing structure, wherein the first stiffness is greater than the second stiffness.

8. The medical system of claim 1, wherein the bearing structure defines a lumen configured to receive the elongate member.

9. The medical system of claim 1, wherein the implantable medical device is configured to position in an atrium of the heart when fixation device affixes the distal end of the implantable medical device to the heart and the distal end of the leadlet implants in the tissue of the heart.

10. The medical system of claim 1, wherein the leadlet carries the second electrode at the distal end of the leadlet.

11. The medical system of claim 1, wherein the fixation device is configured to resist motion of the implantable medical device in a proximal direction when fixation device affixes the distal end of the implantable medical device to the heart.

12. The medical system of claim 1, wherein the implantable medical device comprises a housing, wherein the housing supports the return electrode, and wherein the implantable medical device carries the first electrode on a distal end of the housing.

13. The medical system of claim 1, wherein the leadlet comprises a tip configured to penetrate the tissue to form a puncture sized to enable the leadlet to be inserted therethrough.

14. The medical system of claim 1, further comprising a delivery catheter defining a catheter lumen, wherein the delivery catheter defines a lumen opening to the catheter lumen at a distal end of the delivery catheter, and wherein the catheter lumen and the lumen opening are sized to allow the implantable medical device, the leadlet, and the fixation device to translate through the catheter lumen and through the lumen opening.

15. A medical system comprising:
   an implantable medical device including a housing, wherein the housing carries a first electrode on a distal end of the housing, and wherein the housing carries one or more return electrodes, wherein the housing is configured to be positioned within a heart;
   a leadlet including a proximal end and a distal end, wherein the proximal end is attached to the housing, wherein the distal end is configured to penetrate tissue of the heart, wherein the leadlet carries a second electrode, and wherein a body of the leadlet between the proximal end and the distal end is configured to flex when the distal end is implanted in the tissue of the heart,
   wherein the leadlet includes a bearing structure defining a lumen configured to receive an elongate member, and wherein the distal end of the leadlet is configured to move in a distal direction when the lumen receives the elongate member and a distal force is exerted on the elongate member;
   circuitry supported by the housing, wherein the circuitry is configured to deliver stimulation signals to the heart using the one or more return electrodes and at least one of the first electrode or the second electrode; and
   a fixation device attached to the implantable medical device, wherein the fixation device is configured to affix the distal end of the implantable medical device to the heart.

16. The medical system of claim 15, further comprising a fixation structure supported by the leadlet, wherein the fixation structure is configured to resist motion of the second electrode in a proximal direction when the distal end is implanted in the tissue of the heart.

17. The medical system of claim 15,
   wherein the leadlet is configured to exhibit a first stiffness when the bearing structure receives the elongate member and a second stiffness when the elongate member is displaced from the bearing structure, and
   wherein the first stiffness is greater than the second stiffness.

18. The medical system of claim 15, wherein the circuitry is configured to sense signals from the heart using one or more of the first electrode, the second electrode, or the one or more return electrodes.

19. A method comprising:
   affixing, using a fixation device, an implantable medical device to a heart, wherein the implantable medical device carries a first electrode and a return electrode, wherein the implantable medical device is configured to be positioned within the heart;
   receiving, by a bearing structure of a leadlet, an elongate member, wherein a proximal end of the leadlet is attached to the implantable medical device, and wherein a distal end of the leadlet is configured to move in a distal direction when the bearing structure receives the elongate member and a distal force is exerted on the elongate member; and
   penetrating, using the distal end of a leadlet, tissue of the heart, wherein a body of the leadlet between the proximal end and the distal end is configured to flex when the distal end is implanted in the tissue of the heart, and wherein the leadlet carries a second electrode.

20. The method of claim 19, further comprising delivering, using circuitry within the implantable medical device, stimulation signals to the heart using at least one of the first electrode or the second electrode.

* * * * *